United States Patent [19]

Lückers

[11] Patent Number: 4,601,658

[45] Date of Patent: Jul. 22, 1986

[54] METHOD OF MEASURING THE WATER CONTENT OF CHARGES IN A SHAFT FURNACE

[75] Inventor: John Lückers, Plainevaux, Belgium

[73] Assignee: Centre de Recherches Metallurgiques-Centrum Voor Research in de Metallurgie, Brussels, Belgium

[21] Appl. No.: 640,441

[22] Filed: Aug. 13, 1984

[30] Foreign Application Priority Data

Aug. 11, 1983 [LU] Luxembourg .............................. 84958

[51] Int. Cl.[4] .............................................. F27D 19/00
[52] U.S. Cl. .......................................... 432/37; 73/19; 266/99; 266/144; 422/62; 422/68
[58] Field of Search .................. 110/185, 349; 432/37; 236/15 E; 73/19; 266/99, 144; 422/62, 68

[56] References Cited

U.S. PATENT DOCUMENTS

| 3,177,700 | 4/1965 | Sier | 73/19 |
| 3,293,902 | 12/1966 | Kraus | 73/19 |
| 3,522,035 | 7/1970 | Putman | 73/19 |
| 3,946,228 | 3/1976 | Biermann | 73/19 X |
| 3,949,590 | 4/1976 | Boillot | 73/19 |
| 4,305,906 | 12/1981 | Mikasa et al. | 73/19 X |

Primary Examiner—Albert J. Makay
Assistant Examiner—Steven E. Warner
Attorney, Agent, or Firm—Holman & Stern

[57] ABSTRACT

A method of measuring the water content of charge materials in a shaft furnace, such as a blast furnace, wherein a known quantity of material is introduced into the shaft furnace, the gases emerging from the throat of the shaft furnace are analyzed; and the results of this analysis are used to calculate the value of the water content of the charged material.

3 Claims, No Drawings

METHOD OF MEASURING THE WATER CONTENT OF CHARGES IN A SHAFT FURNACE

BACKGROUND OF THE INVENTION

1. Technical Field of the Invention

The present invention relates to a method of measuring the water content of charges in a shaft furnace, such as a blast furnace, for example.

The invention can be applied to shaft furnaces in general, the following description being based on blast furnaces for the sake of clarity and thus should not be construed in a limiting manner.

The operation of a shaft furnace such as a blast furnace may be simplified to a large extent by taking into account the fact that, on the one hand, a charge composed of ores and coke—these are discharged in such a way that they form superposed layers—is introduced at the top and, on the other hand, that at the bottom there are injected oxidants and fuels suitable for stimulating the reduction of the ore; while this reaction occurs reloading is performed as required.

It can be easily understood that the control of the blast furnace requires familiarity both with the chemical nature and the physical state (water content, size grading . . . ) of the various elements which are introduced thereinto.

Furthermore, it is understood that the regulating of the operations of the blast furnace is the more reliable, the greater the accuracy of the data regarding the characteristics of the products charged.

Currently one of the problems is in determining as accurately as possible the water content of the charged materials and in particular that of the coke.

2. Description of the Prior Art

Among the existing measuring methods the most common can be classed in two broad categories: on the one hand, those making use of neutron backscatter probes and, on the other, those based on infrared rays.

The apparatus in the first category, i.e. with neutron backscatter probes, are generally placed at weighing hoppers through which the material passes before being taken up by a device which raises it to the top of the blast furnace.

In the particular case of coke, the degree of inaccuracy is at least plus or minus 1%, which is high when it is considered that the humidity of coke often only varies between 2 and 8%. The measurements are falsified, on the one hand, by the fact that these apparatus react by measuring all the hydrogen contained in the material and are therefore affected not only by the water, but also by the carbonates, hydrocarbons, volatile materials, etc. present in the charge examined, and, on the other hand, by the fact that the measurement is taken in the weighing hopper, and thus it should be taken very rapidly since the coke charge does not remain there for very long; this results in a lack of counting time, i.e. an error resulting from the statistical nature of the measuring process.

The second category comprises the apparatus which use the principle of infrared sensors. These sensors are disposed in such a manner that they examine the material, for example when it is conveyed on belts, and measure by picking up the rays reflected by the material. The degree of inaccuracy is at least 1.5%. The measuring process is greatly affected by, and is therefore dependent on, the size grading, color, visible or "apparent" surface, etc., and in fact only measures the humidity of the surface.

It is known that at present the working processes in blast furnaces and therefore in shaft furnaces in general utilize various devices which analyze not only the charge products (coke, ores . . . ) and the injected elements (forced air, hydrocarbons, coal . . . ) but also the products discharged from the blast furnace, such as the gases collected in the blast furnace throat.

The applicant has observed an unexpected effect, i.e. that by carefully combining various operations for measuring the characteristics of the products entering and leaving the blast furnace, it is possible to calculate therefrom the water content of the charges, for example of the coke, without this water content itself actually being measured. This observation is the basis of the method of the present invention.

OBJECTS OF THE INVENTION

It is therefore an object of the present invention to provide a new and improved method of measuring the water content of charged materials in a shaft furnace, in particular in a blast furnace.

It is another object of the present invention to provide a method of the type referred to which does not involve the disadvantages previously mentioned and which provides measurement with a degree of accuracy which is greater than that of the said two prior art methods mentioned above.

DISCLOSURE OF THE INVENTION

The present invention provides a method of measuring the water content of the charge materials in a shaft furnace, such as a blast furnace, for example, wherein a known quantity of material is introduced into the shaft furnace; the gases emerging from the throat of the shaft furnace are analyzed; and the results of this analysis are used to calculate the value of the water content of the charged material.

It is understood that the operation is carried out under the normal working conditions of a shaft furnace, for example a blast furnace, i.e. equipped with the usual devices for providing information on the ore, coke, blast air, fuels, analysis of the gases collected in the furnace throat, etc. . . . , but possibly without directly measuring the water content of the charged materials, for example of the coke, which measurement would be less accurate than the value provided by the above method.

DESCRIPTION OF THE PREFERRED EMBODIMENTS

In accordance with a first variant of the method of the present invention, the measurement of the water content of the charged material is calculated from the variation of a value proportional to the water content of the gases collected in the throat of the shaft furnace, possibly the measurement of the water content.

In accordance with a further variant, the development of the water content of the gases collected in the throat of the tank furnace is followed before, during and after the introduction of the charge.

In accordance with a preferred embodiment of the above variant in which a value proportional to the water content of the gases collected in the throat of the shaft furnace, or the measurement of this water content, is recorded in a manner which may or may not be continuous, the variation of the value recorded by graphic surfacing, numerical analysis or any other method is evaluated; the water content of the gases leaving the throat is determined by calculation or comparison for example with data tables or by any other method; the flow rate of the above-mentioned gases is determined; the above values (water content, flow rate and analysis of the gas in the throat) obtained are measured so as to define the quantity of water corresponding to the charged material and, by relating this quantity of water to the characteristics of the charged material, in particular to its hydrogen content, the water content of this material is calculated. In particular, the flow rate of the gases discharged from the throat can be determined either by a direct measurement or by establishing a nitrogen balance from the analysis of these gases and the flow rate of the blast air introduced into the shaft furnace.

Preferably, in the method of the invention, before proceeding with the analysis of a sample of the gas collected in the throat of the shaft furnace in order to determine its water content, this sample is rarified by mixing it with a gas which may or may not be inert, for example nitrogen.

I claim:

1. A method of measuring the water content of charge materials in a shaft furnace, comprising the steps of introducing a known quantity of material into the shaft furnace; analyzing the gases emerging from the throat of said shaft furnace; and utilizing the results of said analysis to calculate the value of the water content of the charged material;

the measurement of the water content of the charged material being calculated from the variation of a value proportional to the water content of the gases collected in the throat of the shaft furnace;

the development of the water content of the gases collected in the throat of the shaft furnace being followed before, during and after the introduction of the charge.

2. The method according to claim 1, in which a value proportional to the water content of the gases collected in the throat of the shaft furnace or the measurement thereof is recorded in a manner which is optionally continuous, wherein the variation of the value recorded is evaluated; there is determined therefrom the water content of the gases emerging from the furnace throat; the flow rate of the above-mentioned gases is determined; and said values of water content, flow rate and analysis of the gas in the throat obtained are combined so as to define the quantity of water corresponding to the charged material and, by relating said quantity of water to the characteristics of the charged material, the water content of said material is determined.

3. The method according to claim 1, wherein before proceeding with the analysis of a sample of the gas collected in the throat of the shaft furnace in order to determine its water content, said sample is rarified by mixing it with a gas which is optionally inert.

* * * * *